(12) United States Patent
Furutani et al.

(10) Patent No.: US 7,608,424 B2
(45) Date of Patent: Oct. 27, 2009

(54) PROCESS FOR PRODUCTION OF A RECOMBINANT PROTEIN AND A FUSION PROTEIN

(75) Inventors: Masahiro Furutani, Mishima-gun (JP); Junichi Hata, Mishima-gun (JP); Akiko Togi, Mishima-gun (JP)

(73) Assignee: Sekisui Chemical Co., Ltd., Osaka (JP)

( * ) Notice: Subject to any disclaimer, the term of this patent is extended or adjusted under 35 U.S.C. 154(b) by 0 days.

(21) Appl. No.: 11/837,795

(22) Filed: Aug. 13, 2007

(65) Prior Publication Data

US 2008/0081361 A1 Apr. 3, 2008

Related U.S. Application Data

(62) Division of application No. 10/451,883, filed as application No. PCT/JP01/11438 on Dec. 26, 2001, now Pat. No. 7,276,355.

(30) Foreign Application Priority Data

Dec. 26, 2000 (JP) ............................. 2000-395740

(51) Int. Cl.
*C12P 21/04* (2006.01)
(52) U.S. Cl. .................................................... 435/69.1
(58) Field of Classification Search ........................ None
See application file for complete search history.

(56) References Cited

FOREIGN PATENT DOCUMENTS

| WO | WO 93/13200 A1 | 4/1993 |
|---|---|---|
| WO | WO 00/66756 A1 | 11/2000 |
| WO | WO 00/75346 A1 | 12/2000 |
| WO | WO 01/83804 A2 | 11/2001 |

OTHER PUBLICATIONS

Furutani et al. An Engineered Chaperonin Caging a Guest Protein: Structural Insights and Potential as a Protein Expression Tool. Protein Science, 2005, vol. 14, pp. 341-350.*

Oliveira et al., "Recombinant Brucella Abortus Proteins That Induce Proliferation and Gamma-Interferon Secretion by CD4+ T cells from Brucella-Vaccinated Mice and Delayed-Type Hypersensitivity in Senstized Guinea Pigs", Cellular Immunology, 1996, vol. 172, pp. 262-268.

(Continued)

*Primary Examiner*—Suzanne M. Noakes
(74) *Attorney, Agent, or Firm*—Sughrue Mion, PLLC

(57) ABSTRACT

This invention provides a recombinant protein expression system using a host and cell-free translation system, and is capable of universally expressing a large amount of any protein as soluble protein, while preventing toxicity in hosts, formation of inclusion bodies, and decompositions with proteases. Such may be achieved by expressing the desired protein as a fusion protein with chaperoning, such as about 60 kDa molecular chaperons, 60 kDa heat shock proteins, or thermosomes, and accommodating the desired protein inside of a stereostructure of a chaperonin. The present invention provides a process for producing a protein, which comprises transcribing and translating a gene containing a gene encoding the linked chaperonin subunits and a gene encoding a desired protein thereby synthesizing a fusion protein having the desired protein linked via a peptide linkage to the linked chaperonin subunits.

7 Claims, 8 Drawing Sheets

OTHER PUBLICATIONS

Zondlo et al., "Monomer-Haptamer Equilibrium of the *Escherichia coli* Chaperonin GroES", Biochemistry, 1995, vol. 34, pp. 10334-10339.

Ishii et al., "Production of MBP (Maltose Binding Protein)-GroES Fusion Protein and Utilization to Stimulate GroEL-Medicated Protein Refolding", Journal of Fermentation and Bioengineering, 1998, vol. 85, No. 1, pp. 69-73.

Andrew Hayhurst, "Improved Expression Characteristics of Single-Chain Fv Fragments when Fused Downstream of the *Escherichia coli* Maltose-Binding Protein or Upstream of a Single Immunoglobuln-Constant Domain", Protein Expression and Purification, vol. 18, No. 1, Feb. 2000, pp. 1-10.

Rachel B. Kapust et al., "*Escherichia coli* Maltose-Binding Protein is Uncommonly Effective at Promoting the Solubility of Polypeptides to which it is Fused", Protein Science, vol. 8, No. 9, 1999, pp. 1668-1674.

George Farr et al, "Multivalent Binding of Nonnative Substrate Proteins by the Chaperonin Groel", Cell, vol. 100, No. 5, Mar. 3, 2000, pp. 561-573.

Kazuyo Nishihara et al., "Chaperone Coexpression Plasmids: Differential and Synergistic Roles of Dnak-NdaJ-GrpE and GroEL-GroES in Assisting Folding of an Allergen of Japanese Cedar Pollen, Cryj2, in *Escherichia coli*", Applied and Environmental Microbiology, May 1998, vol. 64, No. 5, pp. 1694-1699.

Duenas M. et al., "Intra-and Extracellular Expression an ScFv Antibody Fragment in *E. coli*: Effect of Bacterial Strains and Pathway Engineering using GroES/L Chaperonins.", Biotechniques, Mar. 1994, vol. 16, No. 3, pp. 476, 477, and 480-483.

* cited by examiner pETD(TCPβ)n (n=1~4)

RBS, ribosome-binding site; CPN, chaperonin; P.P.S.,PreScission protease cleavage sequence; 6His, 6 histidine residues; TAATAG, stop codon 1. control E. coli crude extract, 2. chaperonin monomer, 3. chaperonin dimer, 4. chaperonin trimer, 5. 6. 8. 10. chaperonin tetramer, 7. chaperonin tetramer-HBs fusion protein, 9. chaperonin tetramer-HCVc fusion protein, 11. chaperonin tetramer-AbHC fusion protein (As the antibody, anti-HCVc monoclonal
antibody was used.)

Left: Western blotting, 1. control E. coli crude extract,
2. chaperonin tetramer, 3. chaperonin tetramer-HCVc fusion
protein; right: transfer to membrane and subsequent
staining with Coomassie Brilliant Blue, 1. control E. coli
crude extract, 2. chaperonin tetramer, 3. chaperonin
tetramer-HCVc fusion protein

Fig. 6

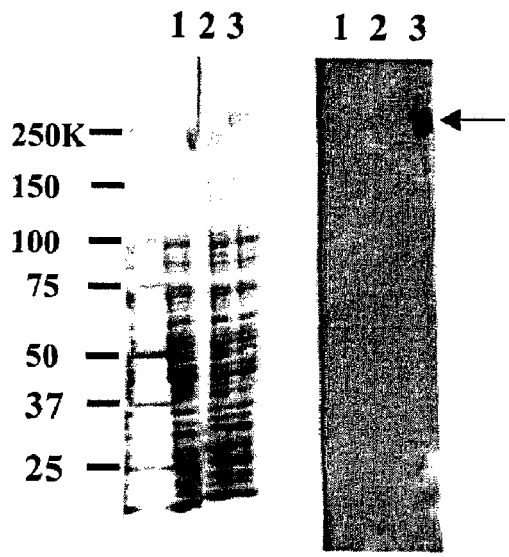

(As the antibody, anti-human antibody Fc polyclonal antibody was used.)

Left: transfer to membrane and subsequent staining with Coomassie Brilliant Blue, 1. control E. coli crude extract, 2. chaperonin tetramer, 3. chaperonin tetramer-AbHC fusion protein; right: Western blotting, 1. control E. coli crude extract, 2. chaperonin tetramer, 3. chaperonin tetramer-AbHC fusion protein pTr(GroE)n (n=1~7)

RBS, ribosome-binding site; CPN, chaperonin GroEL; P.P.S., PreScission protease cleavage sequence; Term., terminator; TAATAG, stop codon 1. control E. coli crude extract, 2. GroEL monomer,
3. GroEL dimer, 4. GroEL trimer, 5. GroEL tetramer,
6. GroEL pentamer, 7. GroEL hexamer, 8. GroEL heptamer

SEQUENCE LISTING

<160> NUMBER OF SEQ ID NOS: 8

<210> SEQ ID NO 1
<211> LENGTH: 1641
<212> TYPE: DNA
<213> ORGANISM: Thermococcus sp. KS-1

<400> SEQUENCE: 1

```
atggcccagc ttgcaggcca gccagttgtt attctacctg agggaactca gaggtacgtt      60
ggaagggacg cccagaggct caacattctt gctgccagga ttatagccga gacggttaga     120
accacccttg gaccaaaggg aatggacaag atgctcgttg acagcctcgg cgacatcgtc     180
atcaccaacg acggtgcaac cattctcgac gagatggaca tccagcaccc tgctgctaag     240
atgatggttg aggttgctaa gactcaggat aaggaggctg tgatggtac tactactgcg      300
gttgttattg ctggtgagct tctgaggaag gctgaggagc ttctcgacca gaacattcac     360
ccgagcataa tcatcaaggg ctacgccctc gcagcagaga aagcccagga aatactcgac     420
gagatagcca aggacgttga cgtcgaggac agggagattc tcaagaaggc cgcggtcacc     480
tccatcaccg gaaaggccgc cgaggaggag agggagtacc tcgctgagat agcagttgag     540
gccgtcaagc aggttgccga gaaggttggc gagacctaca aggtcgacct cgacaacatc     600
aagttcgaga agaaggaagg tggaagcgtc aaggacaccc agctcataaa gggtgtcgtc     660
atcgacaagg aggtcgtcca cccaggcatg ccgaagaggg tcgagggtgc taagatcgcc     720
ctcatcaacg aggcccttga ggtcaaggag actgagaccg acgccgagat caggatcacc     780
agcccggagc agctccaggc cttccttgag caggaggaga agatgctcag ggagatggtc     840
gacaagatca aggaggtcgg cgcgaacgtc gtgttcgtcc agaagggcat tgacgacctt     900
gcccagcact acctggccaa gtacggcata atggcagtca ggagggtcaa gaagagcgac     960
atggagaagc tcgccaaggc cactggagct aagatcgtca ccaacgtccg cgacctcacc    1020
ccggaggacc tcggtgaggc cgagctcgtc gagcagagga aggtcgccgg cgagaacatg    1080
atcttcgtcg agggctgcaa gaacccgaag gcagtgacaa tactcatcag gggcggtacc    1140
gagcacgtcg ttgacgaggt cgagagggcc ctcgaggatg ccgtcaaggt cgtcaaggac    1200
atcgtcgagg acggcaagat cgtcgccgcc ggcggtgctc cggagatcga gctcagcatc    1260
aggctcgacg agtacgcgaa ggaggtcggc ggcaaggagc agctcgccat cgaggccttt    1320
gcagaggccc tcaaggtcat tccgaggacc ctcgccgaga acgccggtct cgacccgatc    1380
gagaccctcg ttaaggtcat cgccgcccac aaggagaagg gaccgaccat cggtgttgac    1440
gtcttcgagg gcgagccggc cgacatgctc gagcgcggcg tcatcgcccc ggtcagggtt    1500
ccgaagcagg ccatcaagag cgccagcgag gccgccataa tgatcctcag gatcgacgac    1560
gtcatcgccc cagcaagct cgagaaggac aaggagggcg gcaagggcgg tagcgaggac    1620
ttcggaagcg atctcgactg a                                              1641
```

<210> SEQ ID NO 2
<211> LENGTH: 681
<212> TYPE: DNA
<213> ORGANISM: Hepatitis B virus

<400> SEQUENCE: 2

```
atggaaaaca ctacttctgg tttcctgggt ccgctgctgg tactgcaggc aggtttcttc      60
ctgctgacac gtatcctcac aattccacag tctctggact cttggtggac ttctctcaat     120
tttctgggtg gtgcaccgac ttgccctggc caaaattctc agtccccaac ctccaatcac     180
tctccaacct cttgccctcc aatttgccct ggctatcgct ggatgtgcct gcgtcgtttt     240
atcatcttcc tcttcatcct gctgctgtgc ctcatcttcc tgctggttct tctggactac     300
caaggtatgc tgccagtttg ccctctgctt ccaggtacat ctaccaccag cactggtcca     360
tgcaagacct gcactattcc tgctcaaggt acctctatgt ttccgtcttg ctgctgcaca     420
aaaccttctg acggtaactg cacttgcatt ccgatcccat cttcctgggc tttcgcacgt     480
tgcctgtggg agtgggcctc tgtccgtttc tcctggctct ctctgctggt gccatttgtt     540
cagtggttcg taggtctgtc tccgactgtt tggctgtctg ttatttggat gatgtggtat     600
tggggtccat ctctgtacaa catcctgtct ccgttctgc ctctgctgcc aattttcttc      660
tgcctttggg tatacattta a                                               681
```

<210> SEQ ID NO 3
<211> LENGTH: 576
<212> TYPE: DNA
<213> ORGANISM: Hepatitis C virus

<400> SEQUENCE: 3

```
atgtctacta acccgaaacc gcagcgtaaa actaaacgta acactaaccg tcgcccacag      60
gacgtcaagt tccctggtgg tggtcagatc gttggtggcg tttacctgct tccacgccgt     120
ggcccacgtc tgggtgtgcg tgcgactcgt aagacttccg agcgctctca acctcgtggt     180
cgtcgtcaac ctatcccgaa ggctcgtcgt ccagagggtc gtgcctgggc tcagccaggt     240
tacccttggc cactctatgg caatgagggc atgggttggg caggttggct cctgtctcca     300
cgcggttccc gtcctagctg gggtccgact gacccacgtc gtcgctctcg taacctgggt     360
aaggtcatcg ataccctcac atgcggcttc gccgacctca tgggttacat tccgctcgtc     420
ggtgccccac tgggtggtgc tgccgtgcc ctggcgcatg gcgtccgtgt tctggaagac      480
ggcgtgaact atgcaacagg taatctgcca ggttgctctt tctctatctt cctcctggct     540
ctgctgtcct gcctgaccat cccagcctcc gcttaa                               576
```

<210> SEQ ID NO 4
<211> LENGTH: 777
<212> TYPE: DNA
<213> ORGANISM: Mus musculus

<400> SEQUENCE: 4

```
atgaaatacc tattgcctac ggcagccgct ggattgttat tactcgctgc ccaaccagcg      60
atggcccagg tgcagctgca ggagtcagga cctggcctgg tggcgccctc acagagcctg     120
tccatcacat gcaccgtctc agggttctca ttaaccggct atggtgtaaa ctgggttcgc     180
cagcctccag gaaagggtct ggagtggctg ggaatgattt ggggtgatgg aaacacagac     240
tataattcag ctctcaaatc cagactgagc atcagcaagg acaactccaa gagccaagtt     300
ttcttaaaaa tgaacagtct gcacactgat gacacagcca ggtactactg tgccagagag     360
agagattata ggcttgacta ctggggccaa ggcaccacgg tcaccgtctc tcaggcggt      420
ggcggatcag gtggcggtgg aagtggcggt ggtgggtctg acatcgagct cacccagtct     480
```

| ccagcctccc tttctgcgtc tgtgggagaa actgtcacca tcacatgtcg agcaagtggg | 540 |
| aatattcaca attatttagc atggtatcag cagaaacagg gaaaatctcc tcagctcctg | 600 |
| gtctattata caacaacctt agcagatggt gtgccatcaa ggttcagtgg cagtggatca | 660 |
| ggaacacaat attctctcaa gatcaacagc ctgaacctg aagattttgg gagttattac | 720 |
| tgtcaacatt tttggagtac tcctcggacg ttcggtggag ggaccaagct ggagtag | 777 |

<210> SEQ ID NO 5
<211> LENGTH: 999
<212> TYPE: DNA
<213> ORGANISM: Homo sapiens

<400> SEQUENCE: 5

| tcgagcgcct ccaccaaggg cccatcggtc ttccccctgg caccctcctc caagagcacc | 60 |
| tctgggggca gcgcggccct gggctgcctg gtcaaggact acttccccga accggtgacg | 120 |
| gtgtcgtgga actcaggcgc cctgaccagc ggcgtgcaca ccttcccggc tgtcctacag | 180 |
| tcctcaggac tctactccct cagcagcgtg gtgaccgtgc cctccagcag cttgggcacc | 240 |
| cagacctaca tctgcaacgt gaatcacaag cccagcaaca ccaaggtgga caagaaagtt | 300 |
| gagcccaaat cttgtgacaa aactcacaca tgcccaccgt gcccagcacc tgaactcctg | 360 |
| gggggaccgt cagtcttcct cttcccccca aaacccaagg acaccctcat gatctcccgg | 420 |
| acccctgagg tcacatgcgt ggtggtggac gtgagccacg aagaccctga ggtcaagttc | 480 |
| aactggtacg tggacggcgt ggaggtgcat aatgccaaga caaagccgcg ggaggagcag | 540 |
| tacaacagca cgtaccgtgt ggtcagcgtc ctcaccgtcc tgcaccagga ctggctgaat | 600 |
| ggcaaggagt acaagtgcaa ggtctccaac agagccttcc cagcccccat cgagaaaacc | 660 |
| atctccaaag ccaaagggca gccccgagaa ccacaggtgt acaccctgcc cccatcccgg | 720 |
| gatgagctga ccaagaacca ggtcagcctg acctgcctgg tcaaaggctt ctatcccagc | 780 |
| gacatcgccg tggagtggga gagcaatggg cagccggaga caactacaa gaccacgcct | 840 |
| cccgtgctgg actccgacgg cccgttcttc ctctacagca agctcaccgt ggacaagagc | 900 |
| aggtggcagc aggggaacgt cttctcatgc tccgtgatgc atgagggtct gcacaaccac | 960 |
| tacacgcaga agagcctctc cctgtctccg ggtaaatga | 999 |

<210> SEQ ID NO 6
<211> LENGTH: 1647
<212> TYPE: DNA
<213> ORGANISM: Escherichia coli

<400> SEQUENCE: 6

| atggcagcta aagacgtaaa attcggtaac gacgctcgtg tgaaaatgct gcgcggcgta | 60 |
| aacgtactgg cagatgcagt gaaagttacc ctcggtccaa aggccgtaa cgtagttctg | 120 |
| gataaatctt tcggtgcacc gaccatcacc aaagatggtg tttccgttgc tcgtgaaatc | 180 |
| gaactggaag acaagttcga aaatatgggt gcgcagatgg tgaaagaagt tgcctctaaa | 240 |
| gcaaacgacg ctgcaggcga cggtaccacc actgcaaccg tactggctca ggctatcatc | 300 |
| actgaaggtc tgaaagctgt tgctgcgggc atgaacccga tggacctgaa acgtggtatc | 360 |
| gacaaagcgg ttaccgctgc agttgaagaa ctgaaagcgc tgtccgtacc atgctctgac | 420 |
| tctaaagcga ttgctcaggt tggtaccatc tccgctaact ccgacgaaac cgtaggtaaa | 480 |
| ctgatcgctg aagcgatgga caaagtcggt aaagaaggcg ttatcaccgt tgaagacggt | 540 |
| accggtctgc aggacgaact ggacgtggtt gaaggtatgc agttcgaccg tggctacctg | 600 |

```
tctccttact tcatcaacaa gccggaaact ggcgcagtag aactggaaag cccgttcatc    660
ctgctggctg acaagaaaat ctccaacatc cgcgaaatgc tgccggttct ggaagctgtt    720
gccaaagcag gcaaaccgct gctgatcatc gctgaagatg tagaaggcga agcggtggca    780
actgctgttg ttaacaccat tcgtggcatc gtgaaagtcg ctgcggttaa agcaccgggc    840
ttcggcgatc gtcgtaaagc tatgctgcag gatatcgcaa ccctgactgg cggtaccgtg    900
atctctgaag agatcggtat ggagctggaa aaagcaaccc tggaagacct gggtcaggct    960
aaacgtgttg tgatcaacaa agacaccacc actatcatcg atggcgtggg tgaagaagct   1020
gcaatccagg gccgtgttgc tcagatccgt cagcagattg aagaagcaac ttctgactac   1080
gaccgtgaaa aactgcagga acgcgtagcg aaactggcag gcggcgttgc agttatcaaa   1140
gtgggtgctg ctaccgaagt tgaaatgaaa gagaaaaaag cacgcgttga agatgccctg   1200
cacgcgaccc gtgctgcggt agaagaaggc gtggttgctg gtggtggtgt tgcgctgatc   1260
cgcgtagcgt ctaaactggc tgacctgcgt ggtcagaacg aagaccagaa cgtgggtatc   1320
aaagttgcac tgcgtgcaat ggaagctccg ctgcgtcaga tcgtattgaa ctgcggcgaa   1380
gaaccgtctg ttgttgctaa caccgttaaa ggcggcgacg gcaactacgg ttacaacgca   1440
gcaaccgaag aatacggcaa catgatcgac atgggtatcc tggatccaac caaagtaact   1500
cgttctgctc tgcagtacgc agcttctgtg gctggcctga tgatcaccac cgaatgcatg   1560
gttaccgacc tgccgaaaaa cgatgcagct gacttaggcg ctgctggcgg tatgggcggc   1620
atgggtggca tgggcggcat gatgtaa                                       1647

<210> SEQ ID NO 7
<211> LENGTH: 567
<212> TYPE: DNA
<213> ORGANISM: Homo sapiens

<400> SEQUENCE: 7
atggccttga cctttgcttt actggtggcc ctcctggtgc tcagctgcaa gtcaagctgc     60
tctgtgggct gtgatctgcc tcaaacccac agcctgggta gcaggaggac cttgatgctc    120
ctggcacaga tgaggagaat ctctcttttc tcctgcttga aggacagaca tgactttgga    180
tttccccagg aggagtttgg caaccagttc caaaaggctg aaaccatccc tgtcctccat    240
gagatgatcc agcagatctt caatctcttc agcacaaagg actcatctgc tgcttgggat    300
gagaccctcc tagacaaatt ctacactgaa ctctaccagc agctgaatga cctggaagcc    360
tgtgtgatac aggggtgggg ggtgacagag actcccctga tgaaggagga ctccattctg    420
gctgtgagga aatacttcca aagaatcact ctctatctga aagagaagaa atacagccct    480
tgtgcctggg aggttgtcag agcagaaatc atgagatctt tttctttgtc aacaaacttg    540
caagaaagtt taagaagtaa ggaatga                                        567

<210> SEQ ID NO 8
<211> LENGTH: 1266
<212> TYPE: DNA
<213> ORGANISM: Homo sapiens

<400> SEQUENCE: 8
atggatgtgc tcagccctgg tcagggcaac aacaccacat caccaccggc tccctttgag     60
accggcggca acactactgg tatctccgac gtgaccgtca gctaccaagt gatcacctct    120
ctgctgctgg gcacgctcat cttctgcgcg gtgctgggca tgcgtgcgt ggtggctgcc    180
```

-continued

```
atcgccttgg agcgctccct gcagaacgtg gccaattatc ttattggctc tttggcggtc      240
accgacctca tggtgtcggt gttggtgctg cccatggccg cgctgtatca ggtgctcaac      300
aagtggacac tgggccaggt aacctgcgac ctgttcatcg ccctcgacgt gctgtgctgc      360
acctcatcca tcttgcacct gtgcgccatc gcgctggaca ggtactgggc catcacggac      420
cccatcgact acgtgaacaa gaggacgccc cggccgcgtg cgctcatctc gctcacttgg      480
cttattggct tcctcatctc tatcccgccc atcctgggct ggcgcacccc ggaagaccgc      540
tcggaccccg acgcatgcac cattagcaag gatcatggct acactatcta ttccaccttt      600
ggagctttct acatcccgct gctgctcatg ctggttctct atgggcgcat attccgagct      660
gcgcgcttcc gcatccgcaa gacggtcaaa aaggtggaga agaccggagc ggacacccgc      720
catggagcat ctcccgcccc gcagcccaag aagagtgtga atggagagtc ggggagcagg      780
aactggaggc tgggcgtgga gagcaaggct ggggggtgctc tgtgcgccaa tggcgcggtg      840
aggcaaggtg acgatggcgc cgccctggag gtgatcgagg tgcaccgagt gggcaactcc      900
aaagagcact tgcctctgcc cagcgaggct ggtcctaccc cttgtgcccc cgcctctttc      960
gagaggaaaa atgagcgcaa cgccgaggcg aagcgcaaga tggccctggc ccgagagagg     1020
aagacagtga agacgctggg catcatcatg ggcaccttca tcctctgctg gctgcccttc     1080
ttcatcgtgg ctcttgttct gccccttctg gagagcagct gccacatgcc caccctgttg     1140
ggcgccataa tcaattggct gggctactcc aactctctgc ttaaccccgt catttacgca     1200
tacttcaaca aggactttca aaacgcgttt aagaagatca ttaagtgtaa cttctgccgc     1260
cagtga                                                                1266
```

PROCESS FOR PRODUCTION OF A RECOMBINANT PROTEIN AND A FUSION PROTEIN

This application is a divisional of U.S. application Ser. No. 10/451,883 (Confirmation No. 3561) filed Oct. 16, 2003 (now U.S. Pat. No. 7,276,355), which is a U.S. National Stage Application of PCT/JP01/11438, filed Dec. 26, 2001; which claims benefit of Japanese Application No. 2000-395740, filed Dec. 26, 2000, the disclosure of each of which is incorporated herein by reference in its entirety.

TECHNICAL FIELD

This invention relates to a process for producing a novel protein, which enables production of a protein hardly synthesized as an active protein by expression of a recombinant protein in a host system or by expression of a protein in a cell-free translation system and which realizes efficient synthesis and purification of a protein, and to a fusion protein.

BACKGROUND ART

Up to now, recombinant protein expression systems in many hosts such as bacteria, yeasts, insects, animal and plant cells, and transgenic animals and plants and cell-free translation systems have been established. Particularly in production of recombinant proteins by mammalian cultured cells, the proteins are subjected to suitable posttranslational modification, and thus this production system is becoming a standard system for production of therapeutic agents. However, the protein synthesis level in this system is lower than in the system with microorganisms as the host, thus necessitating a larger culture chamber, which would cause shortage of production facilities in biotechnology industry pursuing new medicines (Garber, K., Nat. Biotech. 19, 184-185, 2001). Protein production techniques using transgenic animals and plants attempted to improve production efficiency in recent years still do not attain full confidence (Garber, K., Nat. Biotech. 19, 184-185, 2001).

In the recombinant protein expression systems developed so far, it is often difficult to obtain a large amount of active protein. If a desired protein is toxic to the host to a certain degree, synthesis of the protein is inhibited to decrease the expression level. Further, even if the desired protein is expressed as soluble protein, the protein may be decomposed by proteases in the host so that the amount of the protein produced is reduced to a very low level. In addition, even if the desired protein is expressed, the protein may fail to achieve suitable folding, resulting in formation of an inclusion body. In this case, even if the protein is solubilized and folded again, the amount of the finally obtained active protein is very low. Particularly when a cell-free translation system is used, the inclusion body is easily formed.

When the inclusion body is formed, it is attempted to solve this problem by using a method of expressing the protein in the form of a fusion protein with e.g. glutathione-S-transferase (GST) (Smith, D. B., et al., Gene 67, 31-40, 1988), with thioredoxin (LaVallie, E. R. et al., Bio/Technology 11, 187-193, 1993), or with a maltose-binding protein (Guan, C., et al., Gene 67, 21-30), but there are few cases where formation of the inclusion body is suppressed at high efficiency. Alternatively, there is a method wherein a desired protein is co-expressed with a chaperonin i.e. a protein group supporting protein-folding reaction to increase the amount of the desired protein expressed in the soluble fraction (Nishihara et al., Apply. Environ. Microbiol., 64, 1694-1699, 1998), but at present, this method cannot achieve a remarkable increase in the amount of the active protein.

As a method of solving the problem of decomposition of the desired protein by proteases in the host, a method of using a host deficient in a part of protease structural genes, for example in lon, ompT etc. in the case of *E. coli*, has been devised (Phillips et al., J. Bacteriol. 159, 283-287, 1984), there are few cases where the influence of decomposition with proteases can be avoided, while if the host is made deficient in all proteases, other problems can occur, thus failing to essentially solve the problem of decomposition with proteases.

As described above, the conventional protein expression techniques have serious problems such as toxicity to hosts, decomposition with host proteases, and formation of inclusion bodies, and thus the expression level is significantly varied depending on the type of protein to be expressed, and expression conditions for each protein should be examined in trial and error. Accordingly, there is demand for development of techniques for essentially solving the problems described above.

SUMMARY OF THE INVENTION

In view of the foregoing, the object of this invention is to provide a recombinant protein expression system using a host and a cell-free translation system capable of universally expressing a large amount of any proteins as soluble proteins while preventing expression of the toxicity of a desired protein in hosts, formation of inclusion bodies and decomposition with proteases by expressing the desired protein as a fusion protein with a chaperonin subunit, that is, about 60 kDa molecular chaperones, 60 kDa heat shock proteins, or thermosomes and accommodating it certainly in the inside of a stereostructure of chaperonin.

This invention relates to a process for producing a protein, which comprises transcribing and translating a gene containing a gene encoding a chaperonin subunit and a gene encoding a desired protein thereby synthesizing a fusion protein having the desired protein linked via a peptide linkage to the chaperonin subunit.

Preferably, the fusion protein comprises 1 to 20 chaperonin subunits linked to one another and a desired protein linked via a peptide linkage to the N-terminus of the linked chaperonin subunits, the C-terminus of the linked chaperonin subunits, or a linking region of the chaperonin subunits.

In this invention, a gene containing a gene encoding the linked chaperonin subunits and a gene encoding a desired protein may be introduced respectively into 2 different plasmids each capable of coexistence and replication in the same host, and then co-expressed in the same host, or a gene containing a gene encoding the linked chaperonin subunits and a gene encoding a desired protein, and a gene encoding the linked chaperonin subunits only, may be introduced respectively into 2 different plasmids each capable of coexistence and replication in the same host, and then co-expressed in the same host.

Preferably, the desired protein, while being in a state linked via a peptide linkage to the chaperonin subunits, is accommodated in the inside of a chaperonin ring.

The chaperonin ring may have formed a 2-layer structure associated non-covalently via a ring plane or may have assembled into a fibrous structure linked non-covalently via a ring plane or its side.

The process in this invention may have a step wherein the desired protein is cleaved by a restriction protease from the fusion protein having linking region, provided with a sequence to be cleaved with the restriction protease, between the chaperonin subunit and the desired protein. In this case, it is preferable that the linking region between the chaperonin subunit is provided with a sequence to be cleaved with the restriction protease.

The process in this invention may have a step wherein the desired protein is cleaved by CNBr from the fusion protein having linking region, provided with a methionine residue, between the chaperonin subunit and the desired protein.

In this invention, the living thing from which the chaperonin is derived includes bacteria, archaeum, eukaryotes and so on.

In this invention, the fusion protein may be synthesized by a host selected from bacteria, yeasts, animal cells, plant cells, insect cells, animals, plants, or insects, or the fusion protein may be synthesized in a cell-free translation system.

In this invention, it is preferable that the gene encoding a desired protein is cDNA derived from mammalians or a partial gene of mammalian-derived cDNA encoding an amino acid sequence of 6 or more residues.

In this invention, the desired protein includes a heavy chain of an antibody derived from mammalians, a light chain of an antibody derived from mammalians, a Fv region single-chain antibody derived from mammalians or a partial protein of 6 or more residues thereof, viral antigens, 7-transmembrane receptor protein (G-protein-coupled receptor), or cytokines.

According to this invention, there is provided a fusion protein comprising chaperonin subunits and a desired protein, wherein the desired protein while being in a state linked via a peptide linkage to the chaperonin subunits is accommodated in the inside of a chaperonin ring. This invention also encompasses the resulting fusion protein.

The chaperonin ring may have formed a 2-layer structure associated non-covalently via a ring plane, or may have assembled into a fibrous structure linked non-covalently via a ring plane or its side.

BRIEF DESCRIPTION OF THE DRAWING(S)

FIG. 6 shows the results of Western blotting in Example 7.

DETAILED DISCLOSURE OF THE INVENTION

Hereinafter, this invention is described in detail. In this invention, a gene containing a gene encoding chaperonin subunits and a gene encoding a desired protein (referred to hereinafter as gene encoding a fusion protein) is used to produce a fusion protein consisting of the desired protein and the chaperonin subunits.

The above-mentioned chaperonin refers a protein made of subunits each having a molecular weight of about 60 kDa, in a group of proteins generally called molecular chaperones which are induced upon application of stress such as heat shock to cells, to support protein folding and to contribute to structure stabilization in the presence or absence of an energy substance ATP, and the chaperonin occurs in every living thing such as bacteria, archaeum and eukaryotes, and functions in protein folding and protecting proteins from denaturation.

Figure 1:
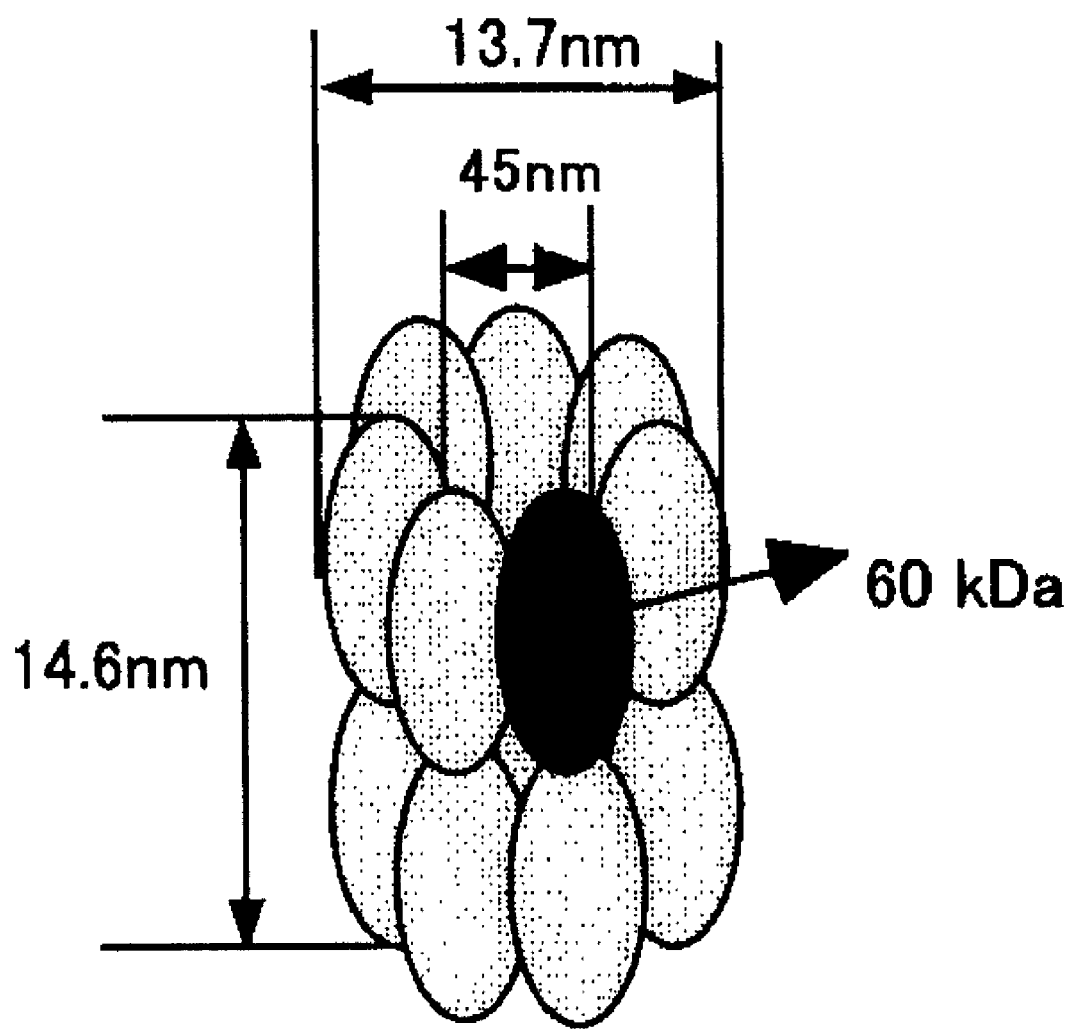
FIG. 1 is a schematic illustration of the stereostructure of *E. coli* chaperonin (GroEL).

Chaperonins have a stereostructure consisting of a two-layer ring (chaperonin ring) composed of 14 to 18 subunits, and for example, *E. coli* chaperonin has a cavity with an inner diameter of 4.5 nm and a height of 14.5 nm (see FIG. 1). The cavity of a 1-layer chaperonin ring has a space in which a 60-kDa spherical protein is sufficiently accommodated. Chaperonin functions in transiently accommodating denatured proteins or folded intermediates of various proteins, and once a folded structure of protein is formed, a chaperonin is conjugated with ATP decomposition to release the accommodated protein from the cavity. Chaperonins derived from bacteria and archaeum can, while maintaining the ring structure, be produced easily in a large amount in the soluble fraction of *E. coli* cytoplasm. This indicates that various kinds of chaperonins derived from different origins can be self-assembled to form a 2-layer ring structure consisting of a 14- to 18-mer.

According to the stereostructure of chaperonins revealed by X-ray crystal structure analysis, the structure is highly flexible with both N- and C-termini of the chaperonin subunit located at the side of the cavity. In particular, at least 20 amino acids of the C-terminus show a highly flexible structure (George et al., Cell, 100, 561-573, 2000).

The chaperonin used in this invention is not particularly limited, and may be derived from bacteria, archaeum and eukaryotes. Further, if the ability of a chaperonin to be self-assembled into a ring structure is maintained, not only wild-type chaperonin but chaperonins with a mutation in the amino acid sequence can also be used. For example, when a mutant with a reduced ability to associate chaperonin subunits is used, a desired protein accommodated therein can be recovered more easily.

The desired protein in the invention is not particularly limited, and may be any disease-related gene products derived from higher animals such as humans and mice, and can be any enzyme groups useful in chemical processes, and examples thereof include proteins such as coat protein, core protein, protease, reverse transcriptase, and integrase encoded by a genome of a pathogenic virus such as type B hepatitis virus, type C hepatitis virus, HIV or influenza virus etc., viral antigens; therapeutic and diagnostic antibodies which are heavy chains in antibodies derived from mammalians, light chains in antibodies derived from mammalians, Fv region single-chain antibodies (scFv) derived from mammalians or partial proteins of 6 or more residues thereof, Fab, (Fab)2, and complete antibodies; 7-transmembrane receptor protein (G protein-coupled receptor); growth factors such as platelet growth factor, blood stem cell growth factor, hepatocyte growth factor, transforming growth factor, nerve growth-trophic factor, fibroblast growth factor and insulin-like growth factor; and cytokines such as tumor necrosis factor, interferon, interleukin, erythropoietin, granulocyte colony stimulating factor, macrophage-colony stimulating factor, albumin and human growth hormone.

The structure of chaperonin is varied depending on the living thing and organeras from which it was derived. The number of subunits constituting a chaperonin ring is 7 in the case of chaperonins derived from bacteria, mitochondria or chloroplast, while the number of subunits constituting a chaperonin ring is 8 or 9 in the case of chaperonin from eucaryotic cytoplasm or archaeum.

In this invention, the ratio of the number of chaperonin subunits to the number of desired proteins in the fusion protein is selected preferably depending on the origin of a chaperonin used. The ratio of the number of chaperonin subunits to the number of desired proteins (number of chaperonin subunits:number of desired proteins) may be in the range of from 1:1 to 12:1, preferably from 1:1 to 9:1. If the number of chaperonin subunits/desired protein is higher than 9, formation of the chaperonin ring is made difficult.

Specifically, when a chaperonin derived from bacteria is used, a fusion protein wherein the number of chaperonin subunits:number of desired protein is 1:1 or 7:1, is preferable for easy formation of a ring structure of the chaperonin, and when an archaeum-derived chaperonin wherein the number of subunits constituting a chaperonin ring is 8 is used, a fusion protein wherein the number of chaperonin subunits:number of desired protein is 1:1, 2:1, 4:1 or 8:1, is preferable for easy formation of a ring structure of the chaperonin. However, there is also the case where other ratios are suitable depending on the shape or molecular weight of the desired protein. For example, when the chaperonin derived from *E. coli* is used, the fusion protein can, even if the number of chaperonin subunits:number of desired protein is 3:1, be associated to form a ring structure consisting of 2 or 3 molecules of the fusion protein.

For example, when an archaeum-derived chaperonin wherein the number of subunits constituting a chaperonin ring is 8 is used, an expressed fusion protein wherein the number of chaperonin subunits:number of desired protein is 2:1 is associated to form a chaperonin ring consisting of 4 molecules of the fusion protein. An expressed fusion protein wherein the number of chaperonin subunits:number of desired protein is 4:1 is associated to form a ring structure consisting of 2 molecules of the fusion protein.

Accordingly, as the ratio of the chaperonin subunits is increased, the molecular size of the desired protein that can be accommodated in the cavity of a chaperonin is increased. To prevent the desired protein from being exposed to host cytoplasm, the number of chaperonin subunits per molecule of the desired protein is preferably 2 or more.

Because chaperonins not only provides a space separated from the external environment but also functions in protein folding, it can fold the desired protein correctly and simultaneously stabilize the structure of the protein. Because the protein-folding reaction of a chaperonin with a single peptide as the substrate protein occurs usually in the ratio of 1:1, the fusion protein is designed preferably such that one molecule of the desired protein is accommodated in a chaperonin ring or a chaperonin, in order to express the folding function of a chaperonin. However, depending on the molecular weight of the desired protein, the desired protein can be correctly folded even if two or more molecules are accommodated.

With respect to the pattern of linkage between the chaperonin subunits and the desired protein in the fusion protein, the desired protein is arranged at the N- or C-terminus of the chaperonin subunits or in a linking region between the chaperonin subunits such that the desired protein can be accommodated in the cavity of a chaperonin. The chaperonin subunits preferably have formed a linkage having 1 to 20 subunits linked therein.

Figure 2:
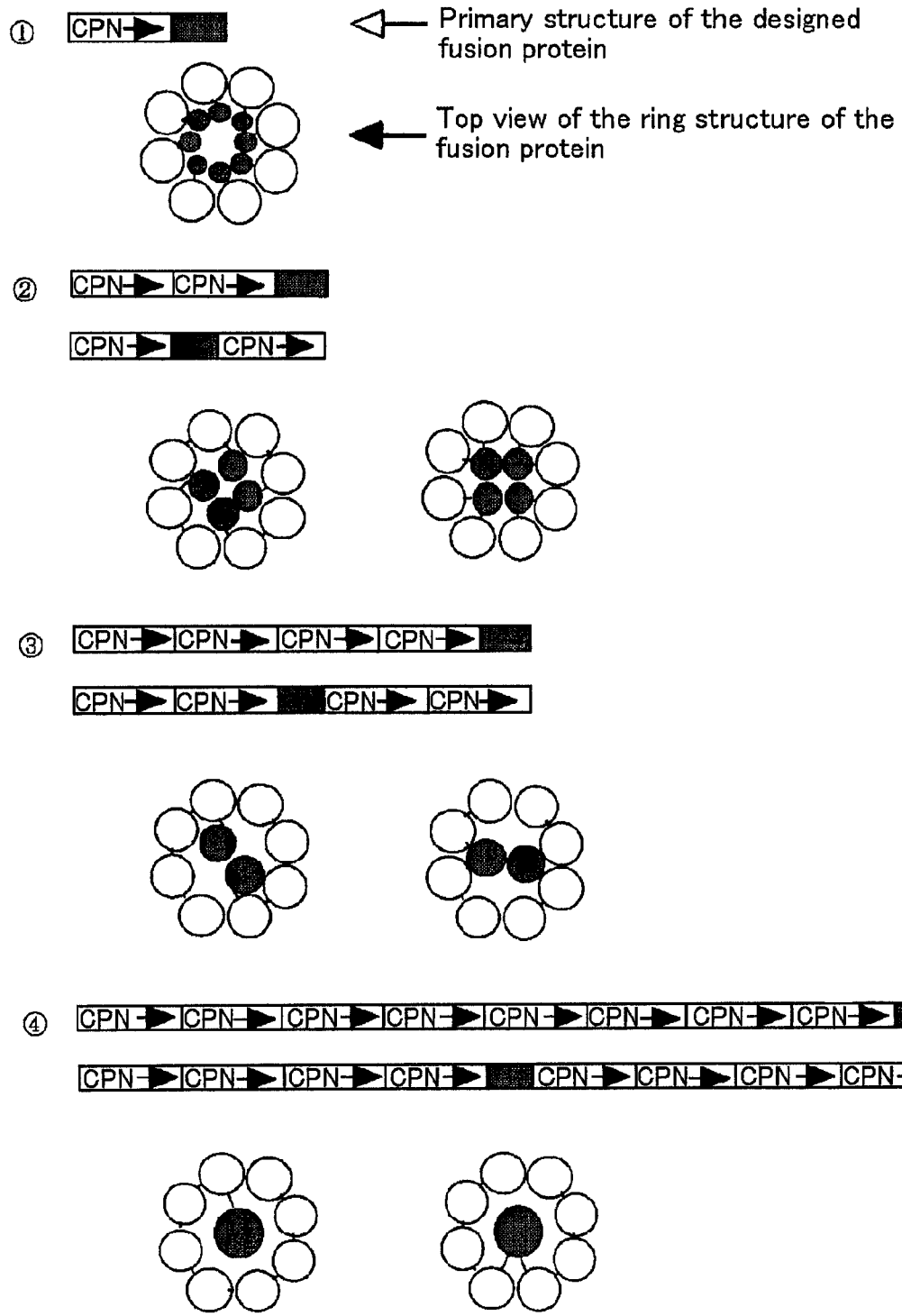
FIG. 2 shows examples of the design of a fusion protein consisting of 8 chaperonin subunits derived from an archaeum and a desired protein.

When the desired protein is extremely toxic to the host or easily digested with host proteases, the desired protein is arranged preferably in a linkage between a plurality of chaperonin subunits. FIG. 2 shows an example of the design of a fusion protein using an archaeum-derived chaperonin composed of 8 subunits.

According to this invention, the desired protein expressed as a fusion protein is accommodated in the cavity of a chaperonin ring and thus protected from the environment in the living body and hardly digested with proteases. Preferably, chaperonin rings are further associated to form a 2-layer structure associated noncovalently via a ring plane.

Even if the desired protein has a property of inhibiting natural mechanism important for the host, the desired protein is separated by the chaperonin ring from the environment in the living body, and thus the protein does not express an inhibitory action on the physiological mechanism in the host. Further, proteins without being associated into a large number of folded protein intermediates as observed upon expression induced with a strong promoter can be fixed separately to the inside of the cavity of a chaperonin ring, thus suppressing the formation of inclusion bodies as observed upon expression in a host or in a cell-free translation system. Chaperonins are synthesized in the soluble fraction of the host cytoplasm or body fluid so that even if the desired protein accommodated in the inside of the chaperonin ring is a membrane-binding or a transmembrane protein, the protein neither destroys the membrane structure in the host nor expresses toxicity to the host. Once accommodated in the same chaperonin ring, any protein can be purified as a fusion protein under identical purification conditions.

When chaperonins are present at a high concentration of not less than 1 mg/mL, two-layer chaperonin rings may further be bound reversibly to one another via a ring plane to assemble into a fibrous structure in the presence of a mg-ATP (Trent, J. D., et al., Proc. Natl. Acad. Sci. U.S.A. 94, 5383-5388, 1997: Furutani, M. et al., J. Biol. Chem. 273, 28399-28407, 1998). Because the fusion protein of the invention is synthesized at a high concentration in the living body, the protein may assemble into a fibrous structure of fusion proteins linked noncovalently via a ring plane or its side so that even if the desired protein is toxic to the host, the accommodation thereof in the chaperonin ring is promoted to achieve high-degree expression of the desired protein. Even if the fusion protein assembles into a fibrous structure, the structure can be dissociated into each 2-layer ring structure by reducing the concentration of the protein through dilution, thus enabling recovery of the desired protein.

In the process for producing a protein according to this invention, a gene encoding a fusion protein is prepared by conventional genetic engineering means such as a method of using restriction enzymes, a PCR method, etc., and by using an expression vector into which the synthesized in the host.

The gene encoding the desired protein, which is used in preparing a gene encoding its fusion protein, is preferably cDNA derived from mammals or its partial gene encoding an amino acid sequence of 6 or more residues.

The host includes, but is not limited to, bacteria such as *E. coli*, other procaryotes, yeasts, insect cells, animal cells such as cultured mammalian cells, plant cells such as cultured plant cells, animals, plants, and insects. In particular, bacteria or yeasts are preferable because of low culture costs, a reduced number of culture days, easy culture procedures, etc. Further, the fusion protein of the invention can also be synthesized as a soluble protein in a cell-free translation system using an extract from bacteria, eukaryotes etc. (Spirin, A. S., Science 11, 2656-2664, 1991: Falcone, D. et al., Mol. Cell. Biol. 11, 2656-2664, 1991).

Generally, when the size of an expression plasmid is kbp or more, the number of copies may be decreased in *E. coli* etc., resulting in a reduction in the amount of desired protein synthesized. For example, when a fusion protein having 8 chaperonin subunits linked therein is produced, the size of an expression plasmid therefor is kbp or more. As a countermeasure, a gene encoding the fusion protein is introduced into 2 different plasmids capable of coexistence and replication in the same host, and then co-expressed in the same host, whereby the amount of the fusion protein expressed can be prevented from being reduced. For example, high expression can be achieved by introducing the same gene producing the same fusion protein into 2 vectors having a different replication region and a chemical resistance gene and transforming the 2 vectors into E. coli etc. in the presence of 2 chemicals, to synthesize the fusion protein.

Further, a gene encoding the fusion protein and a gene encoding the linked chaperonin subunits only may be introduced respectively into 2 different plasmids capable of coexistence and replication in the same host and then co-expressed in the same host. For example, a gene encoding the fusion protein and a gene encoding the linked chaperonin subunits only are introduced respectively into 2 vectors having different chemical resistance and a different replication region and then co-expressed in the presence of 2 chemicals, whereby the structure of a chaperonin can be regulated. For example, in the case of production of a fusion protein wherein the ratio of the number of chaperonin subunits:desired protein is 4:1, a vector containing only a gene for 1 or 2 to 4 linked chaperonin subunits is introduced and co-expressed, whereby the ratio of the number of chaperonin subunits:desired protein is 8:1 can be formed. This method is effective in increasing the expression level because an increase in the size of the plasmid can lead to a reduction in the number of copies to reduce the expression level.

In stead of the introduction of a vector such as plasmid into a host, the fusion protein gene of the invention may be introduced into the chromosome of the host, to express the fusion protein. For example, an expression unit gene consisting of a promoter, a ribosome-binding site, a desired gene, a terminator, a chemical resistance gene etc. can be introduced into the chromosome of a lambda integrase-expressing E. coli host by using the function of lambda integrase in site-specific recombination (Olson, P. et al., Protein Expr. Purif. 14, 160-166, 1998). In the case of yeasts, there is for example a method wherein downstream and upstream sequences of alcohol dehydrogenase (AOX) in methanol-utilizing yeast are used to integrate a desired protein expression unit gene containing an AOX promoter sequence and a terminator into the host chromosome by homologous recombination (Scorer, C. A. et al., Bio/Technology 12, 181-184, 1994). In any cases, a construct having a plurality of expression unit genes linked therein can be introduced into the chromosome to increase the expression level. The expression of a fusion protein having a large molecular weight such as in this invention can be stabilized by expression of the protein through integration of the gene in the chromosome, unlike plasmid expression wherein the number of copies is decreased depending on an increase in the plasmid size.

Because the fusion protein produced in this invention is a gigantic protein having a molecular weight of about 650 to 600 kDa, there can occur cleavage in 2 stages i.e. cleavage of the transcribed mRNA with a specific ribonuclease and cleavage of the translated fusion protein by proteases. For example, when E. coli is used as a host, a host deficient in RNase E gene for ribonuclease involved in decomposition of mRNA can be used to suppress decomposition of polypeptide (Grunberg-Manago, M., Annu. Rev. Gen., 33, 193-227, 1999). For suppressing posttranslational decomposition of mRNA with proteases, it is possible to use a method of expression at a low temperature of 15 to 25° C. or a method of using E. coli deficient in a structural gene for protease as a host, such as Lon, ompT (Phillips et al., J. Bacteriol., 159, 283-287, 1984), Clp or HslVU (Kanemori, M. et al., J. Bacteriol., 179, 7219, 1997).

After the fusion protein is synthesized in the host, the cells are recovered and disrupted to give a supernatant. Because a chaperonin is a gigantic protein having a molecular weight of about 840 to 960 kDa, it can be precipitated by about 40% saturation with sulfate ammonium. The precipitated protein is recovered, dissolved in a suitable buffer and subjected to hydrophobic chromatography or ion-exchange chromatography to recover fractions containing the fusion protein. The recovered solution of the fusion protein is concentrated by ultrafiltration, and the resulting concentrate is subjected to gel filtration using a buffer containing about 5 to 50 mM magnesium chloride and about 50 to 300 mM sodium chloride or potassium chloride as a developing solution, and a peak just after the extrusion limit is recovered, whereby the fusion protein can be purified.

When a tag made of 6 to 10 histidine residues is linked to the N- or C-terminus of the fusion protein, the fusion protein can be recovered easily and efficiently by using a metal (e.g. nickel) chelate column. Further, the fusion protein can be purified rapidly and easily by immune precipitation or affinity chromatography using an antibody against the chaperonin. However, these techniques are combined preferably with ion-exchange chromatography and gel filtration in order to recover only the fusion protein that has formed a ring structure.

When the chaperonin is heat-resistant, the E. coli extract can be treated by heating at 60 to 80° C. to precipitate the majority of proteins derived from E. coli thereby further simplifying purification of the fusion protein. Even if the desired protein itself is not heat-resistant, the protein will not be thermally denatured because it is maintained in the hollow cavity of a chaperonin.

When the fusion protein is purified by any methods described above, the form of the fusion protein can be observed under a transmission electron microscope, and when the desired protein is accommodated in the inside of the chaperonin ring, a ring structure having an external diameter of about 14 to 16 nm, unique to chaperonins, can be observed.

The association of subunits in many kinds of chaperonins is stabilized with magnesium ions and ATP. Accordingly, when the ring structure of the fusion protein is instable, the fusion protein that has formed a ring structure can be efficiently recovered by allowing magnesium and ATP to be present in the purification process. On one hand, when the desired protein only is separated from the resulting fusion protein, a fraction of the fusion protein recovered in the manner described above is treated with EDTA (ethylenediamine tetraacetic acid) and then dialyzed against a buffer free of magnesium and ATP, to remove magnesium and ATP. The interaction between chaperonin subunits is thereby released to destroy the stereostructure of a chaperonin, to expose the desired protein to the outside.

Further, a sequence to be cleaved with a restriction protease such as thrombin, enterokinase or active blood coagulation tenth factor, can be arranged in a linkage between the chaperonin subunit and the desired protein and also in a linkage between the chaperonin subunits, to cleave the desired protein off from the fusion protein with the restriction protease. In this case, when the fraction of the fusion protein recovered in the manner described above is dialyzed, a restriction protease such as thrombin is allowed to act on the dialysate thereby cleaving the desired protein off from the chaperonin subunits.

When the fusion protein of the invention is used as such depending on the object, such a sequence cleaved with proteases may not be present.

After dialysis, the desired protein of high purity can be easily recovered by subjecting it to ion-exchange chromatography or hydrophobic chromatography or to affinity chromatography with an antibody.

When there is no methionine residue in the desired protein, a methionine residue is allowed to be present in a linkage between the chaperonin subunit and the desired protein, whereby the desired protein can be easily cleaved off and released with CNBr from the chaperonin subunit.

When the recovery of the desired protein only is desired, the fusion protein may not be necessarily purified to homogeneity, and the crude purified sample is treated with EDTA, treated with proteases and subjected to purification procedures depending on the desired protein. If there is no methionine in the desired protein so methionine is allowed to present between the chaperonin subunit and the desired protein, then the desired protein can be cleaved off with CNBr from the chaperonin subunit, and therefore the procedure of treatment of the fusion protein with EDTA and subsequent dialysis is not necessary.

This invention also encompasses a process for producing a desired recombinant protein, which comprises synthesizing a fusion protein as described above to produce the fusion protein in the soluble fraction of host cytoplasm, and recovering the desired protein only.

When the desired protein is a membrane-binding protein or a transmembrane protein, the desired protein may be insolubilized by cleaving the desired protein from the chaperonin subunit. In this case, the resulting insolubles are recovered by centrifugation and treated with a nonionic surfactant whose hydrophobic alkyl group is about octyl (8 carbon atoms) to dodecyl (12 carbon atoms), whereby the insolubles are easily solubilized because the diameter of the resulting micelle corresponds approximately to the thickness of the biomembrane. The nonionic surfactant includes, for example, 8-octylglucoside, Triton X-100, Nonidet P-40, Tween 20 etc.

According to this invention, the desired protein can be accommodated certainly as a fusion protein with a chaperonin in the inside of the cavity of a chaperonin ring, to solve problems such as expression of the toxicity of the desired protein to the host, decomposition with proteases, and formation of inclusion bodies, thus permitting it to be expressed as a soluble protein in a large amount. Further, efficient purification is feasible.

BEST MODE FOR CARRYING OUT THE INVENTION

Hereinafter, this invention is described in more detail by reference to the Examples, but this invention is not limited to the Examples.

EXAMPLE 1

Synthesis of *Thermococcus* KS-1 Strain Chaperonin β Subunit Linkage

Figure 3:
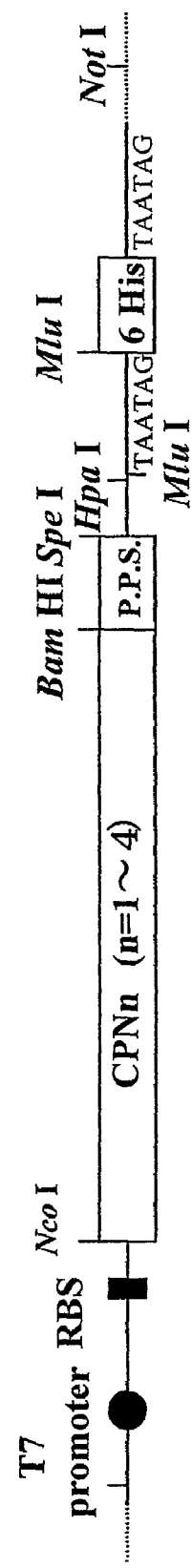
FIG. 3 shows a restriction enzyme map of an expression vector pETD(TCPβ)n (n=1 to 4).
Figure 4:
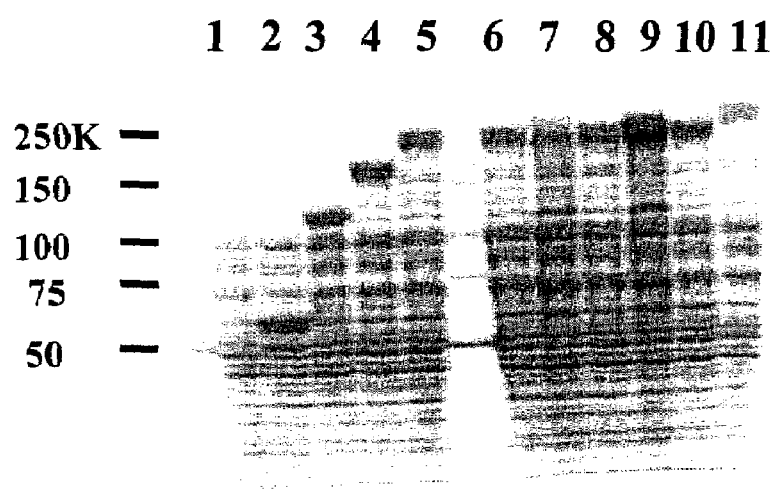
FIG. 4 shows the results of SDS-PAGE of (TCPβ)n (n=1 to 4) and a TCPβ tetramer/desired protein fusion protein.

A chaperonin β-subunit (TCPβ) gene shown in SEQ ID NO:1 was cloned by polymerase chain reaction (PCR) with *Thermococcus* KS-1 strain genome as a template. An expression vector pETD(TCPβ)n (n=1 to 4) having a T7 promoter, wherein a gene fragment having the TCPβ gene was linked 1, 2, 3 and 4 times in one direction, was constructed (FIG. 3). Each expression vector was introduced into *E. coli* BL21 (DE3) strain, which was then cultured at 30° C. for 24 hours in 2XY. T. medium (16 g Bactotrypton, 10 g yeast extract, 15 g/L NaCl) containing carbenicillin, to express a chaperonin β-subunit linkage. After culture, the recovered cells were disrupted by sonication and centrifuged to recover a supernatant which was then analyzed by SDS-PAGE (FIG. 4). From the result of SDS-PAGE, it could be confirmed that (TCPβ)n (n=1 to 4) was expressed in a large amount in the soluble cytoplasmic fraction.

EXAMPLE 2

Observation of a TCPβ Linkage Under a Transmission Electron Microscope pETD(TCPβ)2 and pETD(TCPβ)4 were cleaved with M1uI and subjected to self-ligation to give expression vectors pETDH(TCPβ)2 and pETDH(TCPβ)4 for synthesizing recombinant proteins having 6 histidine residues added to the C-termini of a TCPβ dimer and a TCPβ tetramer respectively (see FIG. 3). After a BL21 (DE3) strain was transformed with the vectors, an extract of the *E. coli* expressing a chaperonin β-subunit linkage was obtained under the same conditions in Example 1. The microbial extract was treated by heating at 75° C. for 30 minutes at a concentration of 5 mg/mL protein, whereby the majority of *E. coli*-derived proteins were denatured and precipitated. The supernatant was recovered by centrifugation and applied onto a nickel chelate Sepharose column. After the column was washed sufficiently with 50 mM Na phosphate buffer (pH 7.0) containing 10 mM imidazole, and the fraction adsorbed onto the nickel chelate Sepharose was eluted with the same buffer containing 500 mM imidazole. As a result of confirmation of the eluted fraction by SDS-PAGE, it was found that a TCPβ dimer and TCPβ tetramer were recovered. After the resulting fraction was dialyzed against 25 mM Tris-HCl buffer (pH 7.5) containing 5 mM $MgCl_2$, the dialysate was separated by anion-exchange chromatography on a TSK gel Super Q-5PW column (Tosoh), whereby the TCPβ2 dimer and TCPβ2 tetramer were purified to homogeneity respectively.

The respective purified preparations were subjected to negative staining with 0.2% uranyl acetate and observed for their form under a transmission electron microscope, and as a result, both of them had formed a ring structure of 15 nm in diameter unique to chaperonins. From this result, it was found that even if the subunits were linked, TCPβ molecules were assembled into a ring structure unique to chaperoning. It is estimated that 4 molecules of TCPβ dimer are assembled into one ring, while 2 molecules of TCPβ2 tetramer are assembled into one ring.

EXAMPLE 3

Synthesis of a TCPβ Tetramer/HBs Antigen Fusion Protein)

A type B hepatitis virus surface antigen (HBs antigen) gene shown in SEQ ID NO:2 was provided at the 5'-terminus thereof with SpeI site and at the 3'-terminus with HpaI site by PCR, and then introduced into pETDH(TCPβ)$_4$ treated previously with SpeI and HpaI, to construct an expression vector pETDH(TCPβ)4·HBs for synthesizing a TCPβ tetramer/HBs antigen fusion protein having 6 histidine residues introduced into the C-terminus. This vector was transformed into a BL21 (DE3) strain, and then the fusion protein was synthesized under the same conditions in Example 1. A soluble fraction of the disrupted *E. coli* cells was separated by SDS-PAGE and analyzed by Coomassie Brilliant Blue, and as a result, a band having a size corresponding to that of the fusion protein was detected (FIG. 4). After SDS-PAGE, the band was transferred onto a blotting membrane and subjected to Western blotting with anti-HBs antigen polyclonal antibody. As a result, the extract of E. coli expressing the TCPβ tetramer only was negative, but in only the extract of the E. coli synthesizing the fusion protein, a positive band corresponding its size (about 260 KDa) was detected. From this result, it was found that the HBs antigen was expressed as a fusion protein with TCPβ tetramer in the soluble fraction of E. coli. In an experiment of expression of HBs antigen only, both the soluble fraction and precipitated fraction of E. coli were negative in the same Western blotting.

(Purification of Recombinant HBs Antigen)

The fusion protein was recovered by a nickel chelate column in the same manner Example 2, and after imidazole was removed by dialysis, the TCPβ tetramer/HBs antigen fusion protein was purified by anion-exchange chromatography on a TSK gel Super Q-5PW column using 5 mM $MgCl_2$ as a developing solution. Further, the presence of HBs antigen was confirmed by Western blotting with anti-HBs antigen polyclonal antibody. The resulting fusion protein was observed under a transmission electron microscope, and as a result, it had formed a ring structure unique to chaperonins. From this result, it was estimated that 2 molecules of the fusion protein were assembled into a ring structure. The recovered fraction was incubated in the presence of 1 mM 2Na EDTA (disodium ethylenediaminetetraacetate), treated with PreScission protease (Amersham Pharmacia Biotec) and incubated at 4° C. for diel. The formed insolubles were recovered by centrifugation, and then dissolved in 1.0% β-octyl glucoside. The HBs antigen in the resulting solubilized material was detected by an EIA kit for measurement of HBs antigen "Enzygnost-HbsAg monoclonal" (Hoechst Bering Diagnostic). As a result of analysis by Western blotting, a band having a molecular weight corresponding to about 25-kDa HBs antigen was specifically detected. From this result, it was found that the recombinant HBs antigen can be excised from chaperonin with a restriction protease. Further, it could be estimated that about 40 mg HBs antigen per L of the E. coli culture solution is expressed in the soluble fraction.

EXAMPLE 4

Co-expression of a Fusion Protein wherein the Number of Chaperonin β-subunits:Number of HBs Antigens is 2:1 and a Chaperonin β-subunit 2 Times Linkage From pETDH(TCPNβ)2 (ampicillin-resistant) prepared in Example 2, an expression unit of (TCPNβ)2 containing T7 promoter was recovered by cleavage with BglII and NotI. This expression unit was cloned in pACYC184 plasmid (Nippon Gene) to construct pATH(TCPNβ)2 (chloramphenicol-resistant). pETDH(TCPNβ)2 and pATH(TCPNβ)2 were transformed into E. coli in an LB agar medium containing ampicillin (100 μg/mL) and chloramphenicol (15 μg/mL), and 10 growing colonies were inoculated into 2×YT liquid medium (16 g Bactotrypton, 10 g yeast extract, 5 g/L NaCl) and cultured at 30° C. for diel in the presence of ampicillin (100 μg/mL) and chloramphenicol (34 μg/mL).

As a result of confirmation of protein expression in the resulting microorganism by SDS-PAGE, the expression of an about 145-kDa fusion protein and an about 120-kDa chaperonin β-subunit dimer could be confirmed. Further, only a band corresponding to 145 KDa was detected by Western blotting with anti-HBs antigen polyclonal antibody. From an extract of the E. coli, a fraction containing the fusion protein was recovered by a nickel chelate column in the same manner as in Example 2. After imidazole was removed by dialysis, the fraction containing the fusion protein was purified by anion-exchange chromatography with a TSK gel Super Q-5PW column. As a result of observation of the resulting protein under a transmission electron microscope, a ring structure unique to chaperonins had been formed. From the results of SDS-PAGE and Western blotting, it could be judged that when only a fusion protein wherein the number of chaperonin β-subunits number of HBs antigens was 2:1 was expressed as the control, its expression level was significantly lower than by the co-expression method. From this result, it was considered that the fusion protein wherein the number of chaperonin β-subunits:number of HBs antigens was 2:1 and the chaperonin β-subunit 2-times linkage are assembled into a ring structure whose cavity accommodates the HBs antigen thereby enabling expression of a large amount of the HBs antigen, but when the fusion protein only is expressed, formation of the ring structure is difficult due to steric hindrance, so the toxicity of HBs antigen to E. coli occurs, thus suppressing expression. According to the expression method in this example, it could be estimated that about 70 mg HBs antigen is expressed in the soluble fraction per L of the E. coli culture solution. The expression level was improved according to the expression method in this example, as compared with synthesis of the TCPβ tetramer/HBs antigen fusion protein (Example 3).

EXAMPLE 5

Synthesis of a TCPβ Tetramer/HCV Core Antigen Fusion Protein

Figure 5:
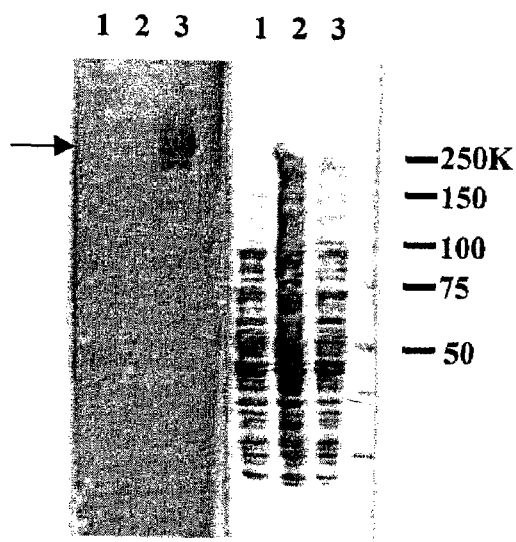
FIG. 5 shows the results of Western blotting in Example 5.

A type C hepatitis virus core antigen (HCVc antigen) gene shown in SEQ ID NO:3 was provided at the 5'-terminus thereof with SpeI site and at the 3'-terminus with HpaI site by PCR, and then introduced into pETDH(TCPβ)4 treated previously with SpeI and HpaI, to construct an expression vector pETDH(TCPβ)4·HCVc for synthesizing a TCPβ tetramer/HCVc antigen fusion protein. This vector was transformed into a BL21 (DE3) strain, and then the fusion protein was synthesized under the same conditions in Example 1. A soluble fraction of the disrupted E. coli cells was separated by SDS-PAGE and analyzed by staining with Coomassie Brilliant Blue, and as a result, a band having a size corresponding to that of the fusion protein was detected (FIG. 4). After SDS-PAGE, the band was transferred onto a blotting membrane and subjected to Western blotting with anti-HCVc antigen monoclonal antibody. As a result, the extract of E. coli expressing the TCPβ tetramer only was negative, but in only the extract of E. coli synthesizing the fusion protein, a positive band corresponding its size (about 260 KDa) was detected (FIG. 5). From this result, it was found that the HCVc antigen was expressed as a fusion protein with TCPβ tetramer in the soluble fraction of the E. coli. In an experiment of expression of HCVc antigen only as the control, the precipitated fraction of E. coli was positive in the same Western blotting, but the soluble fraction was negative. From this result, it was found expressed as an inclusion body, the HCVc antigen can be expressed as a fusion protein with chaperonin β-subunit tetramer in the soluble fraction. The fusion protein was purified by a nickel chelate column and a TSK gel Super Q-5PW column in the same manner Example 3. The resulting fusion protein was observed under a transmission electron microscope, and as a result, it had formed a ring structure unique to chaperoning. From this result, it was estimated that 2 molecules of the fusion protein are assembled into a ring structure. The recovered fraction was incubated in the presence of 1 mM 2Na EDTA and dialyzed against 50 mM K phosphate buffer (pH 7.0). The dialysate was treated with PreScission protease (Amersham Pharmacia Biotec) and incubated at 4° C. for diel. Thereafter, the reaction solution was fractionated by a TSK gel Super Q-5PW column. A 96-well micro-titer plate was coated with the protein in each fraction, then blocked with bovine serum albumin and washed 3 times with PBS-T buffer (10 mM Na phosphate buffer, pH 7.5, 0.8% sodium chloride, 0.05% Tween 20). Then, human positive serum or human negative serum diluted with PBS-T buffer was added to and reacted with it. After washing with PBS-T buffer, it was reacted with peroxidase-labeled human IgG antibody. After the reaction was finished, each well was washed 4 times with PBS-T buffer, and a substrate coloring solution containing phenyl diamine and hydrogen peroxide was added to and reacted with it. After the reaction was terminated by adding 4 N sulfuric acid, its absorbance at 490 nm was measured. As a result of analysis of the detected HCVc antigen-positive fraction by SDS-PAGE, it was found that the HCVc antigen, about 22 kDa, had been purified to almost homogeneity. From the foregoing, it was found that the recombinant HCVc antigen could be excised from chaperonin by a restriction protease. Further, it could be estimated that in the expression method in this example, about 80 mg HCVc antigen per 1 L of the *E. coli* culture solution is expressed in the soluble fraction.

EXAMPLE 6

Synthesis of a TCPβ Tetramer/Anti-lysozyme scFv Antibody Fusion Protein

A mouse-derived anti-chicken lysozyme single-chain antibody (anti-HEL-single chain Fv antibody: HscFv) gene shown in SEQ ID NO:4 was provided at the 5'-terminus thereof with SpeI site and at the 3'-terminus with HpaI site by PCR, and then introduced into pETDH(TCPβ)4 treated previously with SpeI and HpaI, to construct an expression vector pETDH(TCPβ)4·HscFv for synthesizing a TCPβ tetramer/HscFv fusion protein. This vector was protein was synthesized under the same conditions in Example 1. A soluble fraction of the disrupted *E. coli* cells was separated by SDS-PAGE and analyzed by staining with Coomassie Brilliant Blue, indicating a band having a size corresponding to that of the fusion protein. After SDS-PAGE, the sample was transferred onto a blotting membrane and subjected to Western blotting with anti-6HIs monoclonal antibody, that is, an antibody recognizing 6 histidine residues, and as a result, the extract from the *E. coli* expressing the TCPβ tetramer only was negative, but in the extract from the *E. coli* synthesizing the fusion protein, a positive band corresponding to the size this result, it was found that HscFv is expressed as a fusion protein with TCPβ tetramer in the soluble fraction of the *E. coli*. As a result of an experiment of expression of only HscFv as the control, a precipitated fraction of the *E. coli* was positive in the same Western blotting, but the soluble fraction of the *E. coli* was negative. From this result, it was found that although HscFv, when expressed alone, is expressed as an inclusion body, HscFv can be expressed as a fusion protein with chaperonin β subunit tetramer in the soluble fraction. It could be estimated that in the expression method in this example, about 75 mg HscFv is expressed in the soluble fraction per L of the *E. coli* culture solution.

EXAMPLE 7

Synthesis of a TCPβ Tetramer/Human-derived Antibody Heavy Chain Constant Region Fusion Protein A human-derived antibody heavy chain constant region (AbHC) gene shown in SEQ ID NO:5 was provided at the 5'-terminus thereof with SpeI site and at the 3'-terminus with HpaI site by PCR, and then introduced into pETDH(TCPβ)4 treated previously with SpeI and HpaI, to construct an expression vector pETDH(TCPβ)4·AbHC for synthesizing a TCPβ tetramer/AbHC fusion protein. This vector was transformed into a BL21 (DE3) strain, and then the fusion protein was synthesized under the same conditions in Example 1. A soluble fraction of the disrupted *E. coli* cells was separated by SDS-PAGE and analyzed by staining with Coomassie Brilliant Blue, indicating a band having a size corresponding to that of the fusion protein (FIG. 4). After SDS-PAGE, the sample was transferred onto a blotting membrane and subjected to Western blotting with anti-human IgG-Fc antibody, that is, an antibody recognizing a human-derived antibody Fc region, and as a result, the extract from the *E. coli* expressing the TCPβ tetramer only was negative, but in the extract from the *E. coli* synthesizing the fusion protein, a positive band corresponding to the size (about 270 KDa) of the fusion protein was detected (FIG. 6). From this result, it was found that AbHC is expressed as a fusion protein with TCPβ tetramer in the soluble fraction of the *E. coli*. As a result of an experiment of expression of only AbHC as the control, both soluble and precipitated fractions of the *E. coli* were negative in the same Western blotting. From this result, it was found that although AbHC, when expressed alone, is hardly expressed in *E. coli*, AbHC can be expressed as a fusion protein with chaperonin β subunit tetramer in the soluble fraction. Further, it could be estimated that in the expression method in this example, about 75 mg AbHC is expressed in the soluble fraction per L of the *E. coli* culture solution.

EXAMPLE 8

Expression of *E. coli* Chaperonin GroEL Linkage

Figure 7:
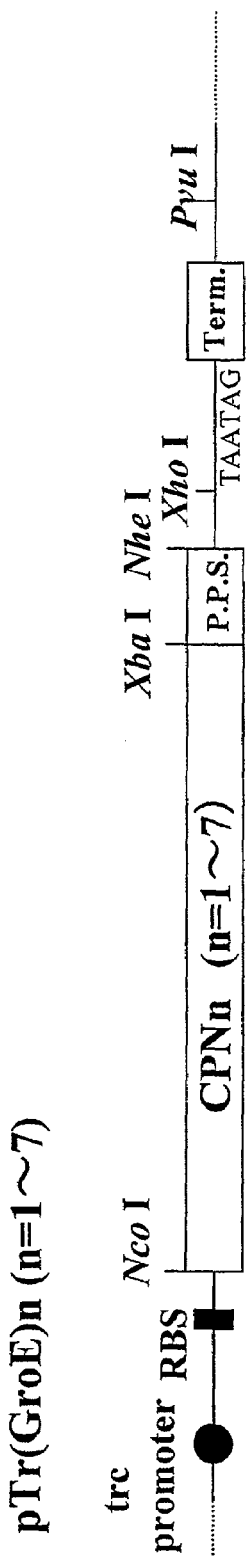
FIG. 7 shows a restriction enzyme map of an expression vector pTr(GroE)n (n=1 to 7).
Figure 8:
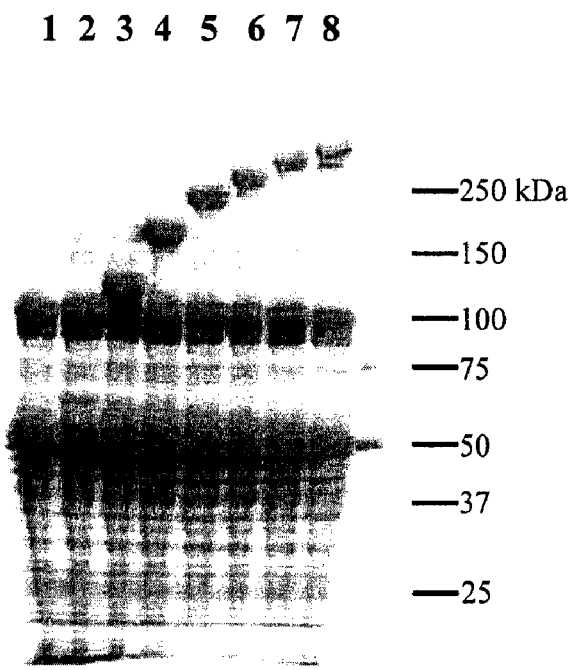
FIG. 8 shows the results of SDS-PAGE of the soluble fraction of *E. coli* wherein an *E. coli* chaperonin GroEL linkage was expressed in Example 8.

An *E. coli* chaperonin GroEL gene shown in SEQ ID NO:6 was cloned by PCR using *E. coli* K12 strain genome as a template. Expression vectors pTr(GroE)$_n$ (n=1 to 7) having a trc promoter, wherein a gene fragment having the GroEL gene was linked 1, 2, 3, 4, 5, 6 and 7 times in one direction, were constructed (FIG. 7). Each expression vector was introduced into *E. coli* BL21 (DE3) strain, which was then cultured at 25° C. for 24 hours in 2XY. T. medium (16 g Bactotrypton, 10 g yeast extract, 15 g/L NaCl) containing carbenicillin (100 µg/mL), to express a % chaperonin β-subunit linkage. After culture, the recovered cells were disrupted by sonication. The supernatant was recovered by centrifugation and then analyzed by SDS-PAGE, and as a result, it could be confirmed that (GroE)n (n=1 to 7) was expressed in a large amount in the soluble fraction (FIG. 8). The recombinant (GroE)7 was purified from the recovered *E. coli* extract by DEAE-Sepharose, TSK gel Super Q-5PW and gel filtration. As a result of observation of the resulting purified preparation under a transmission electron microscope, a ring structure unique to chaperonins was observed. From this result, it was found that even if all subunits are linked, *E. coli* chaperonin GroEL maintains its 7-fold symmetric ring structure.

EXAMPLE 9

Synthesis of an *E. coli* Chaperonin GroEL 7-times Linkage/Human Interferon Fusion Protein A human interferon α2b (INF) gene shown in SEQ ID NO:7 was provided at the 5'-terminus thereof with NheI site and at the 3'-terminus with XhoI site by PCR, and then introduced into pTr(GroE)7 treated previously with NheI and XhoI, to construct an expression vector pTr(GroE)7·INF for synthesizing a GroEL 7-times linkage/human interferon fusion protein. This vector was transformed into a BL21 (DE3) strain, and then the fusion protein was synthesized under the same conditions in Example 8. As the control, expression using pTr(GroE)7 and expression of INF only were also carried out. A supernatant and a precipitated fraction of each *E. coli* extract were separated by SDS-PAGE, then transferred onto a blotting membrane and subjected to Western blotting with anti-INF polyclonal antibody. As a result, a band corresponding to the molecular weight (250 to 260 KDa) of the fusion protein was detected strongly in the soluble fraction from the extract of only the *E. coli* containing pTr(GroE)7·INF. It was found that in expression of INF only, the majority of INF is produced in the insoluble fraction. From the foregoing, it was found that INF is expressed as a soluble protein by expressing INF as a fusion protein with the *E. coli* GrOEL 7-times linkage. From the *E. coli* extract containing pTr(GroE)7·INF, the fusion protein was purified by salting-out, anion-exchange chromatography on DEAE-Sepharose and TSK gel Super Q-5PW columns and gel filtration on Superose 6 (Amersham Pharmacia Biotec). When the resulting purified preparation was observed under a transmission electron microscope, a ring structure unique to chaperonins was found. From the foregoing, it is considered that as a result of the accommodation of each molecule of INF in the cavity of GrOEL, INF is expressed in the soluble fraction.

EXAMPLE 10

Synthesis of an *E. coli* Chaperonin GroEL 7-Times Linkage/Serotonin Receptor Fusion Protein A human serotonin receptor (5HT1A) gene shown in SEQ ID NO:8 was provided at the 5'-terminus thereof with NheI site and at the 3'-terminus with XhoI site by PCR, and then introduced into pTr(GroE)7 treated previously with NheI and XhoI, to construct an expression vector pTrr(GroE)7·5HT1A for synthesizing an *E. coli* chaperonin GroEL 7-times linkage/5HT1A fusion protein. This vector was transformed into an *E. coli* BL21 (DE3) strain, and then the fusion protein was synthesized under the same conditions in Example 8. As the control, expression using pTr(GroE)7 and expression of 5HT1A only were also carried out. A supernatant and a precipitated fraction of each *E. coli* extract were separated by SDS-PAGE, then transferred onto a blotting membrane and subjected to Western blotting with anti-5HT1A polyclonal antibody. As a result, a band corresponding to the molecular weight (about 280 KDa) of the fusion protein was detected strongly in the soluble fraction from the extract of only the *E. coli* containing pTrr(GroE)7·5HT1A. In expression of 5HT1A only, a band having its corresponding size could not be detected in the soluble or insoluble fraction. From the foregoing, it was found that 5HT1A cannot be expressed singly in *E. coli* but can be expressed as a soluble protein by expressing it as a fusion protein with GroEL 7-times linkage. From the extract of the *E. coli* containing pTrr(GroE) 7·5HT1A, the fusion protein was purified by salting-out, anion-exchange chromatography on DEAE-Sepharose and TSK gel Super Q-5PW columns and gel filtration on Superose 6 (Amersham Pharmacia Biotec). When the resulting purified preparation was observed under a transmission electron microscope, a ring structure unique to chaperonins was found. From the foregoing, it is considered that as a result of the accommodation of each molecule of 5HT1A in the cavity of GroEL, 5HT1A is synthesized in the soluble fraction.

EXAMPLE 11

Synthesis of a (TCPβ)4/HBs Antigen Fusion Protein in a Cell-free Translation System For cell-free translation, an expression vector pIV(TCPβ) 4·HBs containing a gene encoding a TCPβ 4-times linkage/ HBs antigen fusion protein was constructed. In the reaction, pIV(TCPβ)4·HBs was added to a reaction solution containing ingredients usually constituting a cell-free translation system, such as RNA polymerase, ribosome, amino acids, nucleotides, aminoacyl tRNA synthase etc., and the mixture was incubated at a constant temperature. After the reaction was finished, the desired fusion protein was purified from the reaction solution to a single protein by nickel chelate chromatography and a TSK gel Super Q-5PW column. When the purified fusion protein was observed under a transmission electron microscope, a ring structure unique to chaperonins was found. In the same manner as in Example 3, the HBs antigen was cleaved off from the purified fusion protein with PreScission protease, and the insoluble HBs antigen was solubilized with β-octylglucoside. This sample was subjected to SDS-PAGE and then subjected to Western blotting with anti-HBs antigen polyclonal antibody, whereby a band of about 25 KDa corresponding to the molecular weight of HBs antigen was detected. When the HBs antigen was expressed alone, the HBs antigen was accumulated in the insoluble fraction and hardly solubilized with β-octylglucoside. As described above, synthesis of HBs antigen as a fusion protein with (TCPβ)4 was also effective in the cell-free translation system.

EXAMPLE 12

Synthesis of a (GroE)7/5HT1A Fusion Protein in a Cell-free Translation System

Cell-free synthesis of a GroEL 7-times linkage/5HT1A fusion protein was carried out in the same manner as in Example 11. As the control, synthesis of 5HT1A alone was also carried out. After the reaction was finished, each sample was subjected to Western blotting with anti-5HT1A polyclonal antibody, and in the fusion protein sample, a band having a size corresponding to the molecular weight (about 280 KDa) of the fusion protein was detected in the soluble fraction. The fusion protein was purified in the same manner as in Example 11 and observed under a transmission electron microscope, showing a ring structure unique to chaperonins. In synthesis of 5HT1A alone, the protein was detected in only the insoluble fraction. From this result, it was found that when 5HT1A is expressed alone, it is expressed as an insoluble protein in the cell-free translation system, but when each molecule of 5HT1A is expressed as a fusion protein with GroEL 7-times linkage, the fusion protein is synthesized as a soluble protein even in the cell-free translation system.

INDUSTRIAL APPLICABILITY

The process for producing a protein and the fusion protein according to this invention are constituted as described above, and are thus useful for increasing the expression level of a protein hardly produced in a large amount and a recombinant protein hardly expressed in the soluble fraction.

What is claimed:

1. A fusion protein consisting of 7 chaperonin subunits and at least one desired protein,
    wherein the 7 chaperonin subunits assemble into a ring structure, and the desired protein is accommodated inside the ring structure, and
    wherein the chaperonin subunit is a bacterial chaperonin subunit.

2. A fusion protein consisting of 2, 4, or 8 chaperonin subunits and at least one desired protein,
    wherein the 8 chaperonin subunits assemble into a ring structure, and the desired protein is accommodated inside the ring structure,
    wherein the chaperonin subunits to desired protein is in a ratio of 2:1, 4:1, or 8:1, and
    wherein the chaperonin subunit is an archaeum chaperonin subunit.

3. A fusion protein consisting of 3 or 9 chaperonin subunits and at least one desired protein,
    wherein the 9 chaperonin subunits assemble into a ring structure, and the desired protein is accommodated inside the ring structure,
    wherein the chaperonin subunits to desired protein is in a ratio of 3:1 or 9:1, and
    wherein the chaperonin subunit is an archaeum chaperonin subunit.

4. The fusion protein according to claim 1, wherein the bacterial chaperonin subunits are *E. coli* GroEL.

5. The fusion protein according to claim 2 or 3, wherein the archaeum chaperonin subunit is *Thermococcus* chaperonin β-subunit (TCPβ).

6. The fusion protein according to claims or 1, 2, or 3, wherein the chaperonin ring has formed a 2-layer structure associated non-covalently via a ring plane.

7. The fusion protein according to claims or 1, 2, or 3, wherein the chaperonin rings have assembled into a fibrous structure linked non-covalently via a ring plane or its side.

* * * * *